United States Patent [19]

Lenarz

[11] Patent Number: 5,320,217

[45] Date of Patent: Jun. 14, 1994

[54] WET SWAB CAPTURED PACKAGE

[75] Inventor: Michael D. Lenarz, Richfield, Minn.

[73] Assignee: Birchwood Laboratories, Inc., Eden Prairie, Minn.

[21] Appl. No.: 79,155

[22] Filed: Jun. 17, 1993

[51] Int. Cl.⁵ .............................. B65D 81/22
[52] U.S. Cl. .................. 206/209; 206/210; 206/361; 206/494; 206/812
[58] Field of Search .............. 132/73, 75; 206/205, 206/209, 210, 229, 361, 494, 812, 37

[56] References Cited

U.S. PATENT DOCUMENTS

| | | | |
|---|---|---|---|
| 2,621,784 | 12/1952 | van Boytham | 206/361 |
| 2,980,940 | 4/1961 | Crowe | 206/229 |
| 3,057,467 | 10/1962 | Williams | 206/361 |
| 3,485,349 | 12/1969 | Chaney, Jr. | 206/812 |
| 3,608,708 | 9/1971 | Storandt | 206/361 |
| 3,674,613 | 7/1972 | Lavigne | 206/812 |
| 3,826,259 | 7/1974 | Bailey . | |
| 4,427,111 | 1/1984 | Laipply . | |
| 4,696,393 | 9/1987 | Laipply | 206/210 |
| 4,701,168 | 10/1987 | Gammons . | |
| 4,762,124 | 8/1988 | Kerch et al. . | |
| 4,800,904 | 1/1989 | Kinseley | 206/812 |
| 4,812,067 | 3/1989 | Brown et al. . | |
| 4,881,278 | 11/1989 | Farah . | |
| 4,938,347 | 7/1990 | Tillman | 206/812 |
| 4,974,730 | 12/1990 | Deruysscher . | |
| 5,046,608 | 9/1991 | Laipply . | |
| 5,111,934 | 5/1992 | Morin . | |

OTHER PUBLICATIONS

Abstract: "Heat Sealing Mechanism with Linearly Movable Seal Bars", Klockner Bartelt Inc., US 5080747 Jan. 14, 1992.

Abstract: "Packaging Machine Adapted to Convert Pouches from Edgewise Advance to Broadwise Advance", Klockner Bartelt Inc., US 5058364 Oct. 22, 1991.

*Primary Examiner*—Jimmy G. Foster
*Attorney, Agent, or Firm*—Vidas, Arrett & Steinkraus

[57] ABSTRACT

A sealed envelope contains a moistened pad that functions as a swab. The pad is secured to the envelope by an intermediate seal line. When the top of the envelope is removed, the pad is exposed. Since the pad is still captively held to the remainder of the envelope, the liquid on the pad may be dispensed by holding the clean, dry bottom of the envelope. The pad functions as a swab and the remainder of the envelope functions as the applicator handle and reservoir.

7 Claims, 3 Drawing Sheets

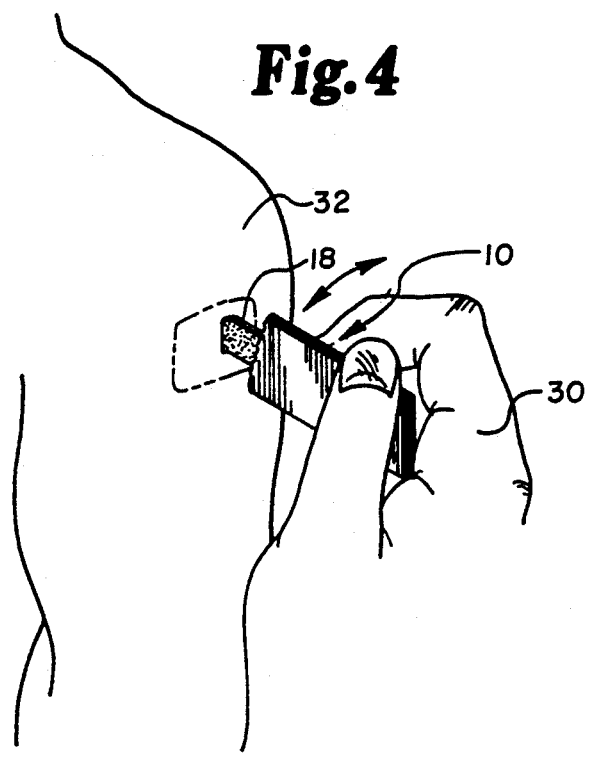
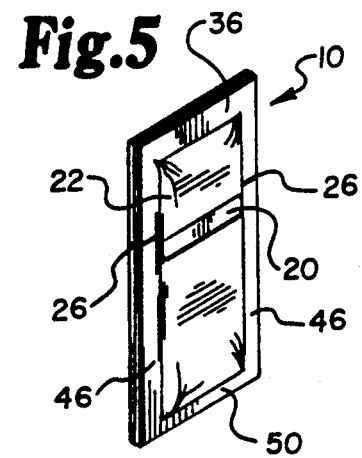
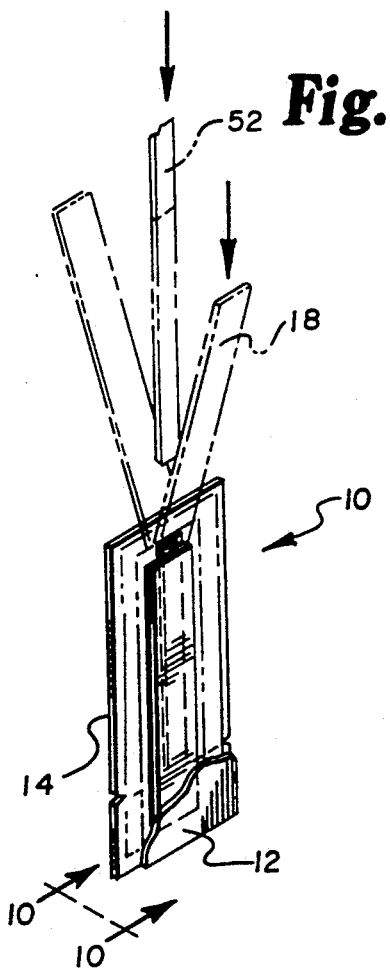
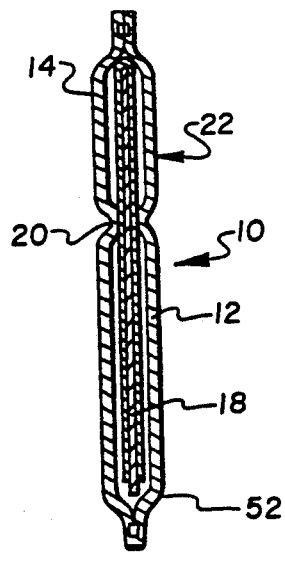
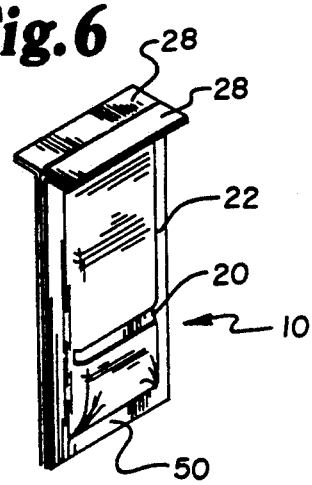

# WET SWAB CAPTURED PACKAGE

BACKGROUND OF THE INVENTION

1. Field of the Invention

This invention relates to a flexible dispensing package for liquids having a wick that acts as an applicator.

2. Description of the Related Art

Previous methods for dispensing controlled amounts of liquid include laminated foil/film packages holding a wooden, plastic or rolled paper stick with a moistened swab end. In the usual manner seen, such packages are foil/plastic film laminates and include a stick with a pad attached to an end. The package around the pad includes an iodine compound useful in disinfecting skin of patients. The package is opened, the swab is removed and the foil/film package is discarded. The stick is then held and used to apply the solution to the area desired. The disadvantage of this package is that it requires two separate operations; swab manufacture and packaging; and it is also relatively expensive to produce and the stick must be held properly to keep it sterile.

Farah, U.S. Pat. No. 4,881,278 shows a toilet seat disinfectant in which a foil package may be pulled open to expose two pads adhered to the foil sides. A folded toilet seat cover is in the upper compartment.

Laipply, U.S. Pat. No. 4,427,111 shows an alcohol wipe sealed in a foil pouch. It shows the prior art packages in which the moist towelette is removed after the foil package is torn open. The Laipply approach is to attach the towelette to the foil such that the package may be peeled open to expose the towelette secured to the inside wall(s) of the foil.

In a later issued patent, U.S. Pat. No. 5,046,608, Laipply adds additional figures showing ways to open the package and to attach the towelette to the inside of the foil. Finally, U.S. Pat. No. 4,800,904 to Kinseley et al shows a nail polish removing pouch in which a moistened towelette is attached to the interior walls of the foil pouch and a finger may be inserted into an opened end to contact the moist towelette.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

The invention provides a sealed package that when opened presents a wet swab that is used by holding the remainder of the package, since the swab is captively held to the package. In its simplest form, a doubled over pad is inserted into a simple liquid-tight pouch, a transverse seal is applied, the desired liquid is added, and the pouch is sealed fluid tight. The improvement consists of the addition of a transverse seal intermediate from the end seals which captures the pad to the package. In this manner, when the top of the pouch is removed, a wet "swab" is exposed which may be used by grasping the remainder of the pouch. This ensures that the user will not have to touch the pad during use and provides an applicator handle.

This construction is very inexpensive to produce and allows the application of the liquids held within without contamination or leakage onto the user. The swab may carry whatever chemicals are needed, in a single use, easy-to-use pouch. The swab may be stiffened according to the needs of the user and chemicals to be used by selection of pad material, thickness, number of folds or addition of a separate stiffener.

BRIEF DESCRIPTION OF THE DRAWINGS

A detailed description of the invention is hereafter described with specific reference being made to the drawings in which:

FIG. 4 shows the exposed swab used to apply liquid;

FIG. 5 shows a variant of the package of FIG. 1 having a slit opening;

FIG. 6 shows a variant of the package of FIG. 1 having a peel opening;

FIG. 9 shows a perspective view, patially broken-away of the package showing a stiffener pushing in the pad; and FIG. 10 shows a cross-sectional view across lines 10—10 of FIG. 9 of the package 10 including a plastic stiffening member 52.

DESCRIPTION OF THE PREFERRED EMBODIMENTS

Figure 1:
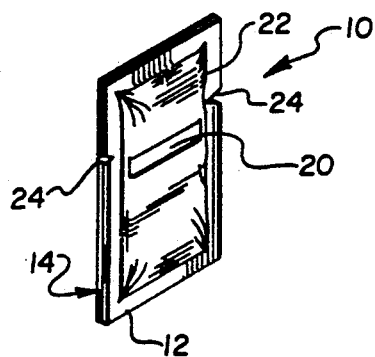
FIG. 1 is a perspective view of the wet swab captured package of the invention.
Figure 2:
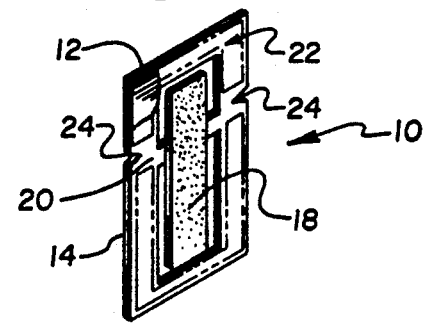
FIG. 2 is a perspective view of the package of FIG. 1 with one side of the foil removed.

The package 10 of the invention is quite simple, yet provides a wet swab applicator at very low cost that is easy to use while keeping the hands free from the wet swab. As best shown in FIGS. 1, 2 and 4, package 10 is envelope-like comprising a front panel 12 and rear panel 14 of suitable fluid impermeable material 16, e.g., metal foil, plastics, and laminates such as aluminum foil/plastic. An absorbent pad 18 is held within the package 10. The package is sealed about its perimeter, either by adhesive or by a physical seal between the front and rear panels.

Figure 3:
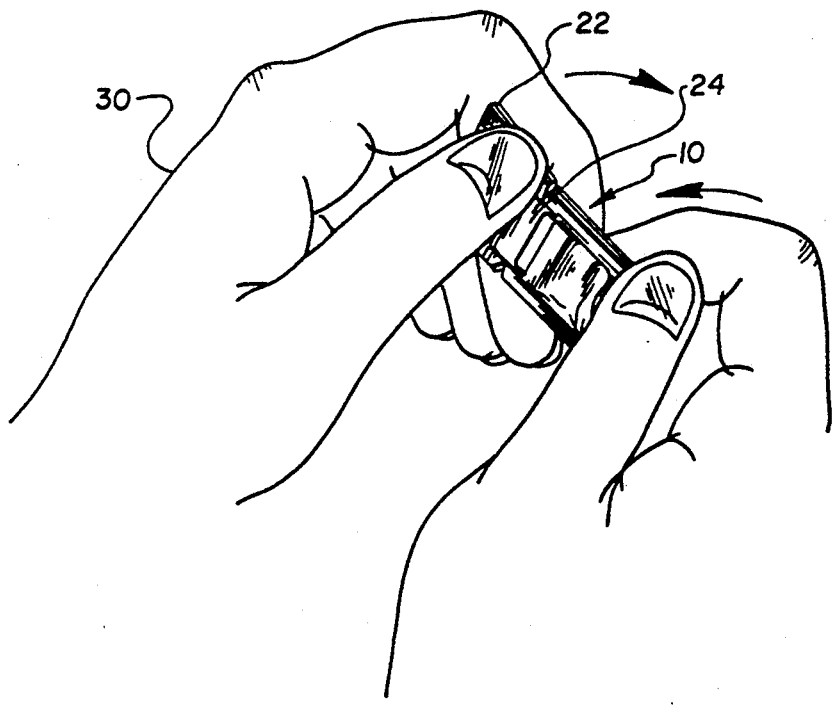
FIG. 3 shows how to remove the top head of the package to expose the swab.

The pad or towlette 18 is held to the package by a transverse seal line 20 across the package 10 which prevents the pad 18 from being readily removed from the package. Means are provided to remove a head portion 22 of the package to expose the pad 18. As shown in FIGS. 2 and 3, the head portion 22 is easily removed by tearing across notched tears 24 formed in the package. Alternatively, the head may be removed by tearing across slits 26 as shown in FIG. 5 or by peeling back the head portion 22 via a peel strip 28 as shown in FIG. 6. Note that in FIG. 6, the head portion 22 is much larger, simply to show that the amount of pad exposed versus retained in the reservoir may vary. Any of the conventional means currently used to open foil packages such as cleaning wipes, catsup packages and the like may be employed. The object is to be able to readily remove the top head portion 22 of the package to expose the wet swab 18 held thereunder.

The pad 18 under the head portion 22 is not attached to the package in any way. The remainder of the pad is attached to the package by the seal line 20 which may be immediately below the tear notch 24 or anywhere therebelow. More than one seal line may be provided, if desired. The space between the transverse seal and the bottom seal acts as a liquid reservoir.

The effect of the joining of the pad to the package below the seal line is to create a very simple, easy to use swab. When the head portion is removed, the swab is exposed. The remainder of the package may be gripped in a hand 30 while the exposed swab 18 is used to supply liquid to a surface. The package 10 may be squeezed to force additional fluid to the swab head. As shown in FIG. 4, the exposed pad 18 is being used as a swab across an arm 32 in the direction of the arrows. The package 10 operates as a holder to hold the swab away from the materials on the swab. This is important to maintain sterility or to prevent applying paint or other liquid carried therein to one's fingers.

Figures 7, 8:
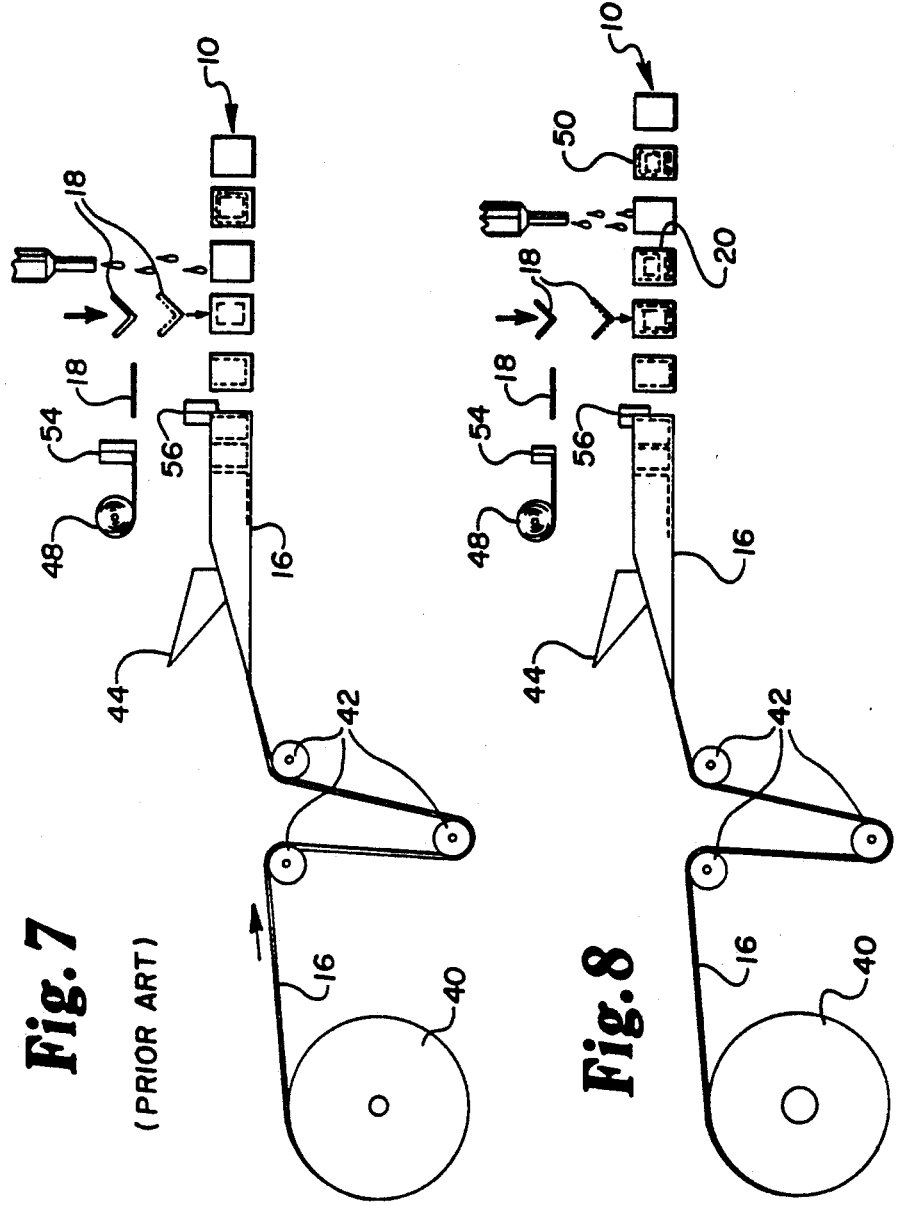
FIG. 7 shows a prior art flow diagram for the process of making foil pouches.
FIG. 8 shows the process for making the package of the invention.

FIG. 7 shows the typical manufacturing process for foil/film laminate packets. A process for making the wet swab captured packages 10 of the invention is shown in FIG. 8, with like reference numerals being used in FIGS. 7 and 8 where the stations are similar. The film or foil 16 to make the package 10 is supplied from a film supply roll 40. The film 16 passes over rollers 42 and is folded in two by a plow 44. The bottom is formed by the fold line and the sides are sealed by a stamping mechanism to form side seals 46. Typically, a bottom seal 36 is made over the fold to improve appearance, minimize leakage and make the package look more uniform. The bottom fold may then be cut off and the remnants of the front panel 12 and rear panel 14 may be used to make the peel strip 28, such that the user simply grasps both panels and peels the package open. Suitable machines for forming the packages of the invention are available from Klockner Bartelt, Inc. and are described in U.S. Pat. Nos. 5,080,747 and 5,058,364.

Most typically, the packages are formed from laminated foil and plastic. The foil provides added strength and rigidity while the thin plastic film provides chemical resistance. Also, the plastic film enables easy heat sealing. The plastic film of one panel is pressed against the other panel and is heated to fuse the plastics together. The combination of heat and pressure, given the proper dwell time for the plastic used provides an excellent seal. Suitable films are available from E. I. DuPont de Nemours and Company of Wilmington, Del., U.S.A. marketed under the trademark Surlyn ®.

It is possible to form the packages 10 of the invention from plastic without foil. Alternatively, foil alone may be satisfactory depending on the liquid to be held. If foil alone is used, a seal may be formed by pattern printing adhesive around the periphery.

The pad or towlette 18 is formed from a towlette supply roll 48 which feeds material to a station where it is cut by a cutter 54 and inserted into the formed package, usually with a mechanical finger that pushes the v-folded pad 18 into the still open package. Liquid is then added and the top seal 50 is formed to complete the package. The individual packets are typically separated from each other after the side and bottom seals have been formed but before filling with towlette or liquid. A cutter 56 (which is shown in the FIGS. before the final package sealing) separates the individual packages.

As shown in FIG. 8, the inventive packets follow a similar manufacturing process. However, after the pad has been inserted into the package a mid seal line 20 is formed across the package to secure the towlette 18 to the package. The remainder of the steps may be identical to the prior art process. It should be noted that in the manufacturing process the bottom seal 36 is actually the last edge to be sealed, and shows in FIG. 8 as the upper edge furthest from the transverse seal 20. This is because the pad 18 is inserted with a finger, folded in a v-shape, such that the fold of the pad 18 will be closest to the top seal 50, adjacent what appears to be the bottom of the package.

If greater swab rigidity is desired, the pad material may be selected to provide greater thickness, have more folds or it may employ additional fibers in the weave that provide stiffening. Alternatively, the finger that inserts the pad may be a strip of plastic 52 that is cut after each pad 18 is inserted to leave a stiffening member surrounded by the pad within the completed package as shown in FIG. 9. In such a package, the swab exposed by removing the head portion 22 is much stiffer.

The wet swab package of this invention may be used to carry almost any liquid. It is expected to find greatest application in dispensing germicides such as povidone-iodine 10%. Other liquids may include paints, paint removers, nail polish or remover, lubricants, solvents, adhesives and ointments. The pad material is chosen based on the properties of the liquid to be dispensed. Absorbent materials will tend to hold the liquid in the pad better than non-absorbent materials. The degree of wicking is controlled by selection of the pad material. For example, application of touch-up paint to an automobile should not allow the paint to drip readily from the package. Rather, the paint should begin to ooze out, in a drop that may be touched to the auto surface, thereby transferring paint. As used herein, "liquid" encompasses compounds having greatly different viscosities and includes gels.

While this invention may be embodied in many different forms, there are shown in the drawings and described in detail herein specific preferred embodiments of the invention. The present disclosure is an exemplification of the principles of the invention and is not intended to limit the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for supplying a liquid from a swab comprising:
   (a) a sealed envelope sealed along its bottom, side and top edges, said envelope including a top and a bottom;
   (b) a pad which functions as a swab, said pad positioned within said envelope and held to said envelope by an intermediate seal across said pad and intermediate between the top and bottom edge of said envelope;
   (c) an intermediate seal across said pad and intermediate the top and bottom edge of said envelope, said intermediate seal holding said pad to said sealed envelope;
   (d) liquid carried within said envelope and capable of wicking through said pad; and
   (e) means for opening the top of said envelope above said intermediate seal, said means for opening comprising envelope weakening structure located on said envelope to facilitate removing a top portion of said envelope above the intermediate seal and at a location to provide an opening, such that said pad, while attached by the intermediate seal, will protrude outwardly of the opening.

2. The device of claim 1 wherein said pad is a folded sheet and the fold line is positioned adjacent the envelope top.

3. The device of claim 2 wherein said opening means comprises weakened regions across said side seals which allow the top end of said envelope to be removed by tearing it off to expose the swab.

4. The device of claim 2 further including a stiffening member inserted between the folded sheets to provide a more rigid swab.

5. The device of claim 1 wherein said liquid is selected from the group consisting of medical liquids, cosmetics, paints, solvents, lubricants and adhesives.

6. The device of claim 5 wherein said medical liquid is a disinfectant.

7. A device for supplying a liquid from a swab comprising:

(a) a sealed envelope sealed along its bottom, side and top edges, said envelope including a top and a bottom;

(b) a pad which functions as a swab, said pad positioned within said envelope and held to said envelope by an intermediate seal across said pad and intermediate between the top and bottom edge of said envelope, wherein said pad is a folded sheet and the fold line is positioned adjacent the envelope top, further including a stiffening member inserted between the folded sheets to provide a more rigid swab;

(c) an intermediate seal across said pad and intermediate the top and bottom edge of said envelope, said intermediate seal holding said pad to said sealed envelope;

(d) liquid carried within said envelope and capable of wicking through said pad; and (e) means for opening the top of said envelope above said intermediate seal such that said pad is still held to said envelope and is exposed when said envelope top is removed.

* * * * *